(12) United States Patent
Rastgaar et al.

(10) Patent No.: US 12,422,016 B2
(45) Date of Patent: Sep. 23, 2025

(54) MAGNETORHEOLOGICAL FLUID CELL SYSTEMS AND METHODS

(71) Applicant: Purdue Research Foundation, West Lafayette, IN (US)

(72) Inventors: Mo Rastgaar, West Lafayette, IN (US); Gabriel Andrés Torres Rivera, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 445 days.

(21) Appl. No.: 17/900,070

(22) Filed: Aug. 31, 2022

(65) Prior Publication Data
US 2023/0061625 A1    Mar. 2, 2023

Related U.S. Application Data

(60) Provisional application No. 63/239,243, filed on Aug. 31, 2021.

(51) Int. Cl.
*F16F 9/53* (2006.01)
*A61F 2/50* (2006.01)
(Continued)

(52) U.S. Cl.
CPC ........ *F16F 9/535* (2013.01); *F16F 2224/025* (2013.01); *F16F 2224/045* (2013.01); *F16F 2230/36* (2013.01); *F16F 2234/00* (2013.01)

(58) Field of Classification Search
CPC ........ F16F 1/361; F16F 2226/04; F16F 1/377; F16F 1/3737; F16F 9/353;
(Continued)

(56) References Cited

U.S. PATENT DOCUMENTS

| | | | | | |
|---|---|---|---|---|---|
| 4,301,459 A | * | 11/1981 | Isayama | ............... | B41J 2/19 347/68 |
| 4,934,669 A | * | 6/1990 | Bourdeau | ............... | F16F 9/16 280/634 |

(Continued)

FOREIGN PATENT DOCUMENTS

CN    101975241 A    2/2011

OTHER PUBLICATIONS

Sikulskyi, S. et al., Magnetorheological Fluid Filled Spring for Variable Stiffness and Damping: Current and Potential Performance. Frontiers in Materials, Mar. 2022, vol. 9.
(Continued)

*Primary Examiner* — Robert A. Siconolfi
*Assistant Examiner* — James K Hsiao
(74) *Attorney, Agent, or Firm* — Purdue Research Foundation

(57) ABSTRACT

A magnetorheological apparatus includes a flexible body formed of an elastomer material, a plurality of cell cavities defined by the flexible body, a magnetorheological (MR) fluid disposed within each cell cavity of the plurality of cell cavities, and a magnetic field inductor positioned adjacent to at least one of the cell cavities. Each cell cavity of the plurality of cell cavities is fluidly encapsulated within the flexible body. The magnetic field inductor is selectively operable to vary a magnetic field, and the MR fluid within the at least one cell cavity is configured to vary a stiffness of the at least one cell cavity in response to the magnetic field.

19 Claims, 10 Drawing Sheets

(51) Int. Cl.
*A61F 2/66* (2006.01)
*F16F 1/36* (2006.01)
*F16F 1/37* (2006.01)

(58) Field of Classification Search
CPC ........... F16F 2224/025; F16F 2224/045; F16F 2230/36; F16F 2234/00; A61F 2/5046; A61F 2/6607; A61F 2002/5004; A61F 2002/503; A61F 2002/5033; A61F 2002/6584
See application file for complete search history.

(56) References Cited

U.S. PATENT DOCUMENTS

| | | | | |
|---|---|---|---|---|
| 5,075,689 | A * | 12/1991 | Hoisington | H04N 1/1912 347/41 |
| 5,963,237 | A * | 10/1999 | Ikkatai | B41J 2/16523 347/85 |
| 5,985,168 | A | 11/1999 | Phule | |
| 6,007,193 | A * | 12/1999 | Kashimura | B41J 2/17593 347/92 |
| 6,823,895 | B2 * | 11/2004 | Hitchcock | F15B 21/065 137/251.1 |
| 8,882,213 | B2 * | 11/2014 | Ghozeil | B41J 2/195 347/17 |
| D736,385 | S | 8/2015 | Nakaya et al. | |
| 11,324,652 | B2 * | 5/2022 | Hollabaugh | A61G 7/1061 |
| 2005/0087409 | A1 * | 4/2005 | Browne | F16F 9/535 188/267.2 |
| 2005/0116194 | A1 | 6/2005 | Fuchs et al. | |
| 2005/0117004 | A1 * | 6/2005 | Lengyel | B41J 2/19 347/87 |
| 2006/0248749 | A1 * | 11/2006 | Ellis | A43B 7/1425 36/28 |
| 2009/0183387 | A1 * | 7/2009 | Ellis | A41D 19/01523 36/28 |
| 2009/0261093 | A1 | 10/2009 | Fullerton et al. | |
| 2010/0234954 | A1 * | 9/2010 | Justis | A61F 2/4425 623/17.12 |
| 2010/0268121 | A1 * | 10/2010 | Kilborn | A61B 5/412 600/587 |
| 2011/0062371 | A1 * | 3/2011 | Marur | H01F 1/36 252/62.51 R |
| 2012/0153531 | A1 * | 6/2012 | Rober | B29C 43/10 264/225 |
| 2016/0167333 | A1 * | 6/2016 | Hethcock, Jr. | B32B 7/12 428/116 |
| 2018/0050500 | A1 * | 2/2018 | Jackson | B29C 64/112 |
| 2019/0006099 | A1 * | 1/2019 | Kobayashi | B29C 45/17 |
| 2019/0249746 | A1 * | 8/2019 | Saley | A41D 1/002 |
| 2021/0059881 | A1 * | 3/2021 | Raymond | A47C 27/15 |
| 2021/0222752 | A1 * | 7/2021 | Büsgen | A47C 27/06 |
| 2022/0230790 | A1 * | 7/2022 | Biegger | G05G 5/03 |

OTHER PUBLICATIONS

Song, B-K. et al., Field-Dependent Stiffness of a Soft Structure Fabricated from Magnetic-Responsive Materials: Magnetorheological Elastomer and Fluid. Materials, 2020, 13, 953.

Park, J. et al., Encapsulations of Magnetorheological Fluids Within 3-D Printed Elastomeric Cellular Structures. IEEE Transactions on Magnetics, vol. 58, No. 8, Aug. 2022 (date of publication Dec. 23, 2021).

Fereidooni, A. et al., Fabrication and Characterization of Highly Controllable Magnetorheological Material in Compression Mode. Journal of Intelligent Material Systems and Structures, 2020, vol. 31 (14) 1641-1661.

Bastola, A. K. et al., 3D Printed Magnetorheological Elastomers. Proceedings of the ASME 2017 Conference on Smart Materials, Adaptive Structures and Intelligent Systems, Sep. 18-20, 2017, SMASIS2017-3732.

Bastola, A. K. et al., Dot-patterned Hybrid Magnetorheological Elastomer Developed by 3D Printing. Journal of Magnetism and Magnetic Materials, 494 (2020) 165825.

Shorter, A. L. et al., Mechanical Impedance of the Ankle During the Terminal Stance Phase of Walking. IEEE Trnasactions on Neural Ssytems and ehabilitation Engineering, vol. 26, No. 1, Jan. 2018.

* cited by examiner

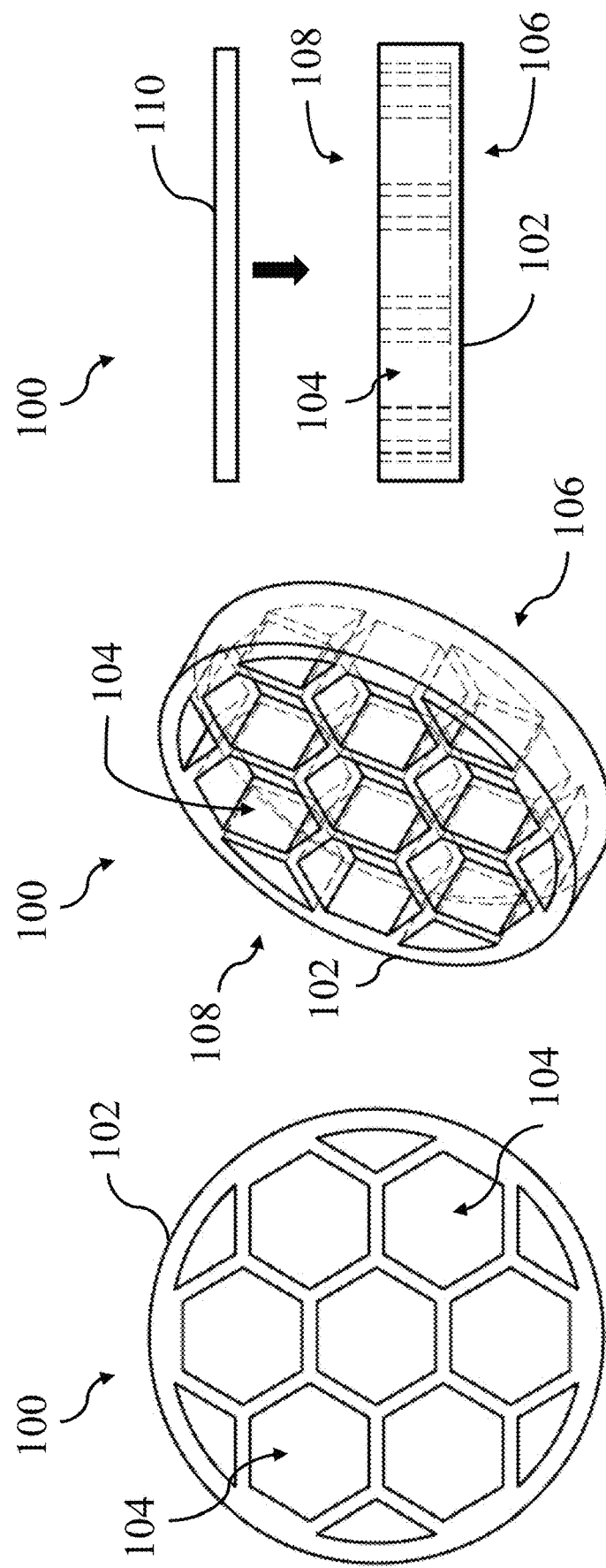

MAGNETORHEOLOGICAL FLUID CELL SYSTEMS AND METHODS

CROSS-REFERENCE TO RELATED APPLICATIONS

This application is related to and claims the priority benefit of U.S. Provisional Application No. 63/239,243, entitled "Magneto-Rheological Fluid/Polymer Cells (MR-Cells)," filed Aug. 31, 2021, the contents of which are hereby incorporated by reference in their entirety into the present disclosure.

TECHNICAL FIELD

The present application relates to magnetorheological-based materials, and specifically to materials formed with magnetorheological fluid elastomer compounds and having selectively variable stiffness.

BACKGROUND

This section introduces aspects that may help facilitate a better understanding of the disclosure. Accordingly, these statements are to be read in this light and are not to be understood as admissions about what is or is not prior art.

Magnetorheological (MR) fluids belong to a class of controllable fluids. The essential characteristic of these fluids is their ability to reversibly change from a free-flowing, linear, viscous liquid to a semi-solid Binghman fluid with a controllable yield strength in milliseconds when exposed to a magnetic field. In the absence of an applied field, MR fluids are reasonably well approximated as Newtonian liquids.

A typical MR fluid has about 20 to about 40 percent by volume of relatively pure, soft iron particles, typically about three to about five microns, suspended in a carrier liquid such as mineral oil, synthetic oil, water, or glycol. A variety of proprietary additives similar to those found in commercial lubricants are commonly added to discourage gravitational settling and promote particle suspension, enhance lubricity, modify viscosity, and inhibit wear. The ultimate strength of the MR fluid depends on the square of the saturation magnetization of the suspended particles. MR fluids made from iron particles typically exhibit maximum yield strengths of 30-90 kPa for applied magnetic fields of 150-250 kA/m (1 Oe·80 A/m). MR fluids are not highly sensitive to moisture or other contaminants that might be encountered during manufacture and use.

Devices combining MR fluids and polymers have been used commercially in dampers, shock absorbers, clutches, and brakes using their flow and shear modes characteristics. However, the use of squeeze-flow magnetorheology mode for such devices has not previously been widely explored.

SUMMARY

Aspects of this disclosure describe devices and fabrication methodologies for MR-cell-based elements that can be integrated with robotic prosthesis (e.g., two degree of freedom robotic prosthesis, or "2-DOF") to allow separation of impedance modulation and torque generation at joints (e.g., ankle joints). Although MR fluid has been used in knee prostheses by utilizing its shear-flow magnetorheology mode to create a damper, the advantageous devices and fabrication methodologies integrate actuators with the squeeze-flow mode of MR fluids to generate a new class of actuators enabling independent impedance modulation and torque control.

Accordingly, multi-cell MR-fluid elastomer compounds are described with improved stiffness characteristics. Particularly, aspects of the improved device can include a flexible body structure formed of a material, in some embodiments including an elastomer. The device can also include a plurality of cell cavities defined by the flexible body, and each cell cavity of the plurality of cell cavities can be fluidly encapsulated within the flexible body. A magnetorheological (MR) fluid can be disposed within each cell cavity of the plurality of cell cavities, and a magnetic field inductor can be positioned adjacent to at least one of the cell cavities. The magnetic field inductor can be selectively operable to vary a magnetic field. The MR fluid within the at least one cell cavity can further be operable to vary a stiffness of the at least one cell cavity in response to the magnetic field.

In some embodiments, the improved device can include a plurality of magnetic field inductors each positioned adjacent to one cell cavity of the plurality of cell cavities. Each magnetic field inductor can be individually operable to provide an individualized magnetic field to vary the stiffness of each respective cell cavity in response to the individualized magnetic field.

Additional aspects of the described embodiments can include a method of manufacturing a magnetorheological device. The method can include various acts such as molding the flexible body, casting the flexible body using an elastomeric material, and inserting the MR fluid into each cell cavity defined by the flexible body. In some methods, inserting the MR fluid can include puncturing the flexible body with a syringe and injecting the magnetorheological fluid. In other aspects of the methods, molding the flexible body can include separately molding a first portion and a second portion, and casting the flexible body can include separately casting the first portion and the second portion. Thereafter, the first portion can be affixed to the second portion such that each cell cavity of the plurality of cell cavities is fluidly encapsulated within the flexible body upon affixing the first portion to the second portion.

This summary is provided to introduce a selection of the concepts that are described in further detail in the detailed description and drawings contained herein. This summary is not intended to identify any primary or essential features of the claimed subject matter. Some or all of the described features may be present in the corresponding independent or dependent claims, but should not be construed to be a limitation unless expressly recited in a particular claim. Each embodiment described herein does not necessarily address every object described herein, and each embodiment does not necessarily include each feature described. Other forms, embodiments, objects, advantages, benefits, features, and aspects of the present disclosure will become apparent to one of skill in the art from the detailed description and drawings contained herein. Moreover, the various apparatuses and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1A depicts a top plan view of a first MR fluid-based apparatus, the first MR fluid-based apparatus having seven fluid cells;

FIG. 1B depicts a front isometric view of the first MR fluid-based apparatus of FIG. 1A, FIG. 1C depicts a side view of the first MR fluid-based apparatus of FIG. 1A, showing the capping layer;

Figure 2A:
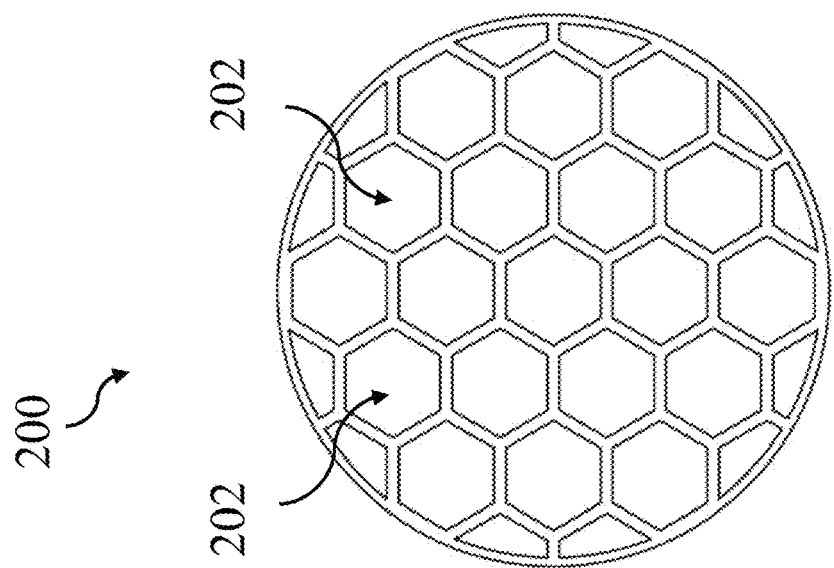
FIG. 2A depicts a top plan view of a second MR fluid-based apparatus, the second MR fluid-based apparatus having 19 fluid cells.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown, or the precise experimental arrangements used to arrive at the various graphical results shown in the drawings.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

The present disclosure describes various embodiments of MR fluid cells formed using elastomer matrices. While many practical applications stand to benefit by such devices, the design and implementation of 2-DOF prosthesis is one particular area of interest and will be described in greater detail herein. However, it should be understood that the advantageous devices and methods described herein are therefore not limited to prosthesis as they would be effective in many other applications as well.

The MR fluid-based elastomer devices described herein are capable of varying or modulating their impedance about multiple axes or within multiple degrees of freedom. In some embodiments, MR fluid-based elastomer devices may be formed by several individual cells arranged as an array or in a geometric pattern such that multiple MR-fluid cells may be separately formed, the MR fluid of each cell is fluidly separated, and each cell is independently manipulated using one or more magnets positioned adjacent to one or more cells.

Shown in FIGS. 1A-1C are one embodiment of a MR fluid-based elastomer device (100). The device (100) includes a main body (102) that forms a plurality of individual cells (104) each configured to be separately filled with MR fluid (not shown). The main body (102) defines a first side (106) that is solidly formed across the diameter of the main body (102) such that each cell (104) is closed, and the main body (102) defines a second side (108) that initially provides open pathways into each cell (104) so each cell (104) may be filled with MR fluid during fabrication phases. The device (100) further includes a cap (110) shaped to be affixed to the second side (108) of the main body (102) such that the open pathways to the cells (104) are all fluidly closed to encapsulate the MR fluid once the cap (110) is affixed in place. While a main body (102) and cap (110) are described as separate portion of the device (100), it should be understood that once the cap (110) is positioned on the main body (102) for use of the device (100), effectively the first side (106) and second side (108) are closed, thus in alternative embodiments of the device (100) may instead be manufactured as a single unitary piece defining multiple cell pockets therein. The main body (102) of the device, and in some embodiments the cap (110) may be formed of a flexible material such as an elastomer. In some embodiments, the elastomer is formed using a silicone rubber compound, while other materials and combinations of materials such as urethane rubber, TPU (e.g., thermoplastic polyurethane), neoprene rubbers, rubbers infused with magnetizable particles (e.g., magnetorheological elastomers) and other elastic matrix materials may be utilized as well. Such a soft elastomer can act as a flexible bladder with little stiffness contribution, thus allowing the majority of the stiffness to come from the magnetized MR fluid and the thinned walled pressure vessel design.

As described above, the device (100) may define a plurality of separate cells (104). While FIGS. 1A-1C illustrate a version whereby the cells (104) are configured in a hexagonal geometric pattern, other alternative patterns (e.g., pentagonal, triangular, circular, square, rectangular) were contemplated. Hexagonal cells (104) are described in the greatest detail herein as a hexagonal pattern provides the least amount of perimeter to surface area ratio for each cell (104), thereby achieving an efficient and effective profile of impedance and stiffness for the application of an ankle prosthesis. Further, hexagonal cells (104) can reduce elastomer column wall thickness and increase magnetorheological fluid packing density. Specifically, each side (112) of the cells (104) may be configured to abut one or more sides (114) of another cell. In the embodiment of FIGS. 1A-1C, each cell defines a side (112) length from approximately 10 to 12 millimeters, with a cell wall (114) thickness from approximately 0.75 to 2 millimeters. In a particular embodiment, a cell wall (114) thickness of 1.3 millimeters enabled consistent manufacturing. Further in the embodiment of FIGS. 1A-1C, a total of seven cells (104) are geometrically grouped, thereby providing seven separately variable MR fluid cells. However, while examples of cell (104) sizes and pluralities are described, it should be understood that any particular application of the novel aspects described herein may require adjustment to the cell (104) sizing and plurality.

Figure 2B:
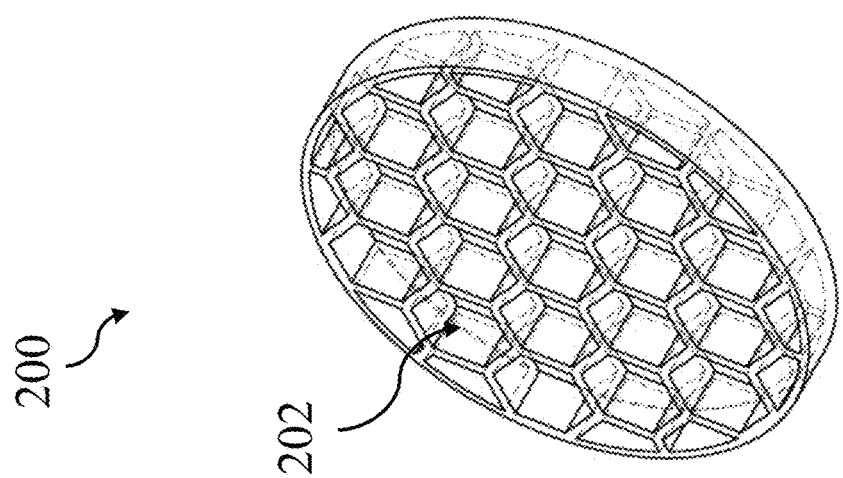
FIG. 2B depicts a front isometric view of the second MR fluid-based apparatus of FIG. 2A.
Figure 2C:
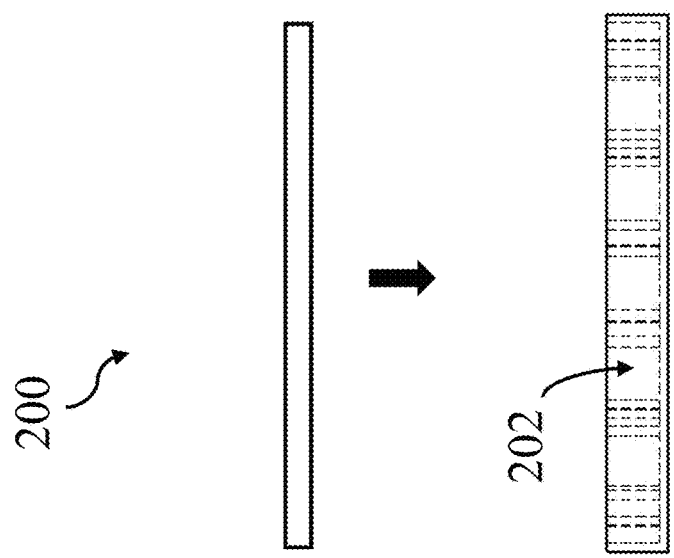
FIG. 2C depicts a side view of the second MR fluid-based apparatus of FIG. 2A, showing the capping layer.
Figure 3A:
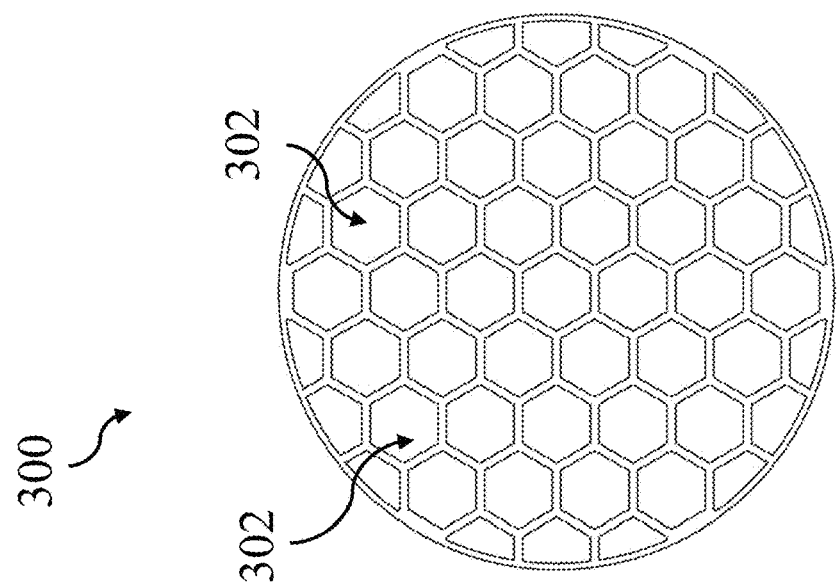
FIG. 3A depicts a top plan view of a third MR fluid-based apparatus, the third MR fluid-based apparatus having 37 fluid cells.
Figure 3B:
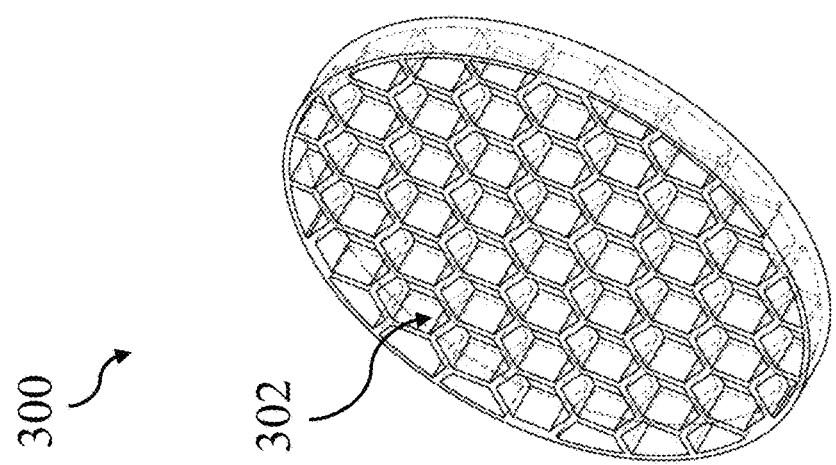
FIG. 3B depicts a front isometric view of the third MR fluid-based apparatus of FIG. 3A.
Figure 3C:
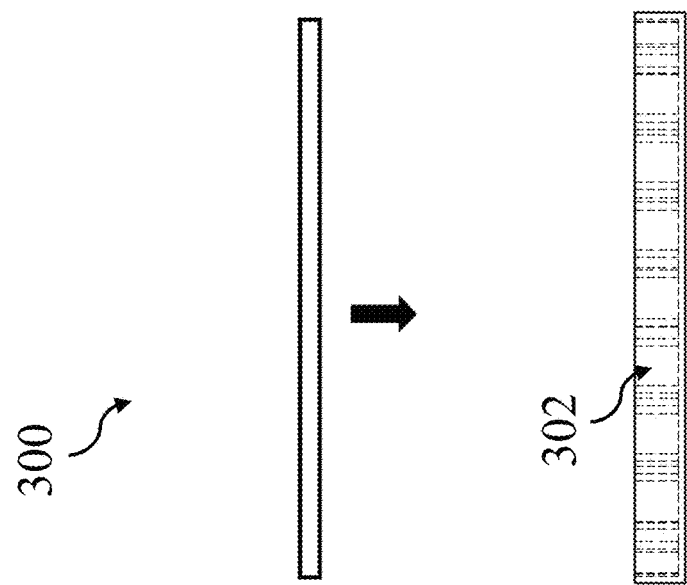
FIG. 3C depicts a side view of the third MR fluid-based apparatus of FIG. 3A, showing the capping layer.

As a first alternative example to the cell (104) plurality, FIGS. 2A-2C show an embodiment of a similar device (200) defining 19 individual cells (202). Additionally, as a second alternative example to the cell (104) plurality, FIGS. 3A-3C show an embodiment of a similar device (300) defining 37 individual cells (302). In other embodiments (not shown), a single cell may be utilized.

Figure 4B:
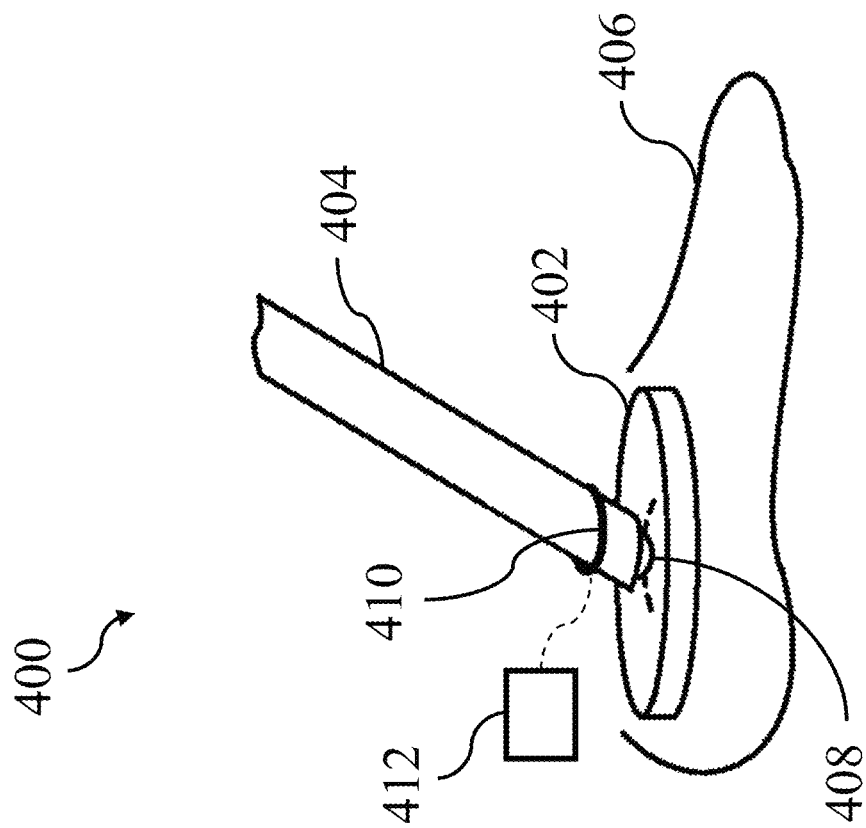
FIG. 4B depicts a schematic diagram of the MR fluid-based apparatus of FIG. 4A, showing a leg portion and foot portion of the ankle prosthetic in a second position.
Figure 4A:
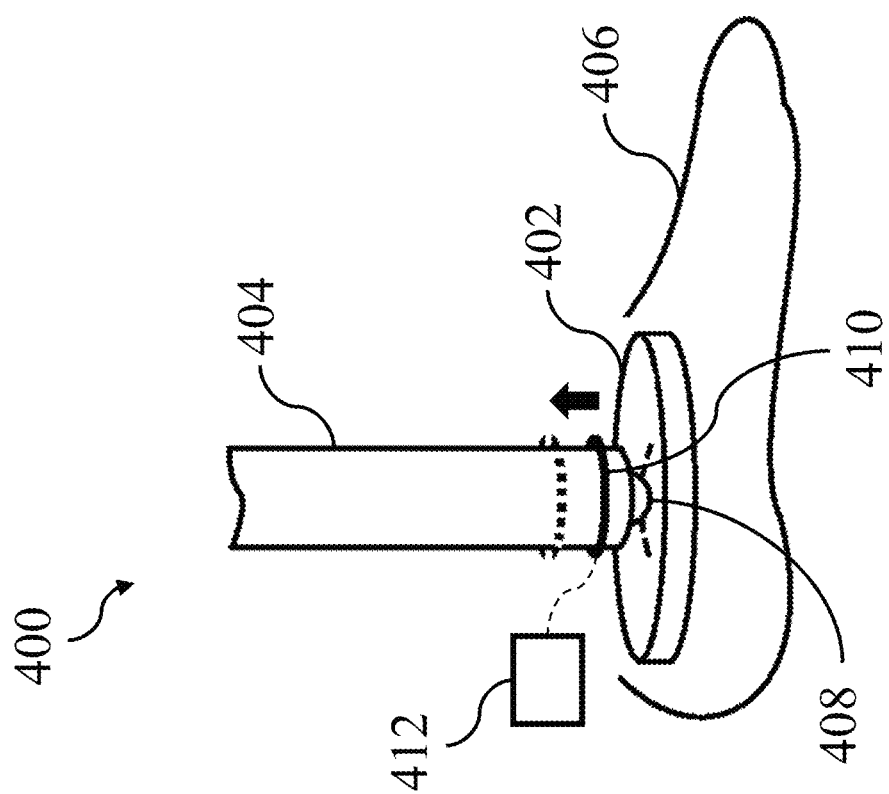
FIG. 4A depicts a schematic diagram of one example practical application of an MR fluid-based apparatus being used within an ankle prosthetic, showing a leg portion and foot portion of the ankle prosthetic in a first position.

Shown in FIG. 4A is one exemplary application (400) of an MR fluid elastomer device (402) being utilized within an ankle prosthetic to selectively provide stiffness variation during use of the ankle prosthetic. MR fluid elastomer device (402) may be formed in accordance with the embodiments of devices (100, 200, 300) described above or the described design variations. Particularly, the device (402) may be movably coupled with a shank or leg portion (404) and a foot portion (406). The leg portion (404) may be configured to couple with a human or animal body (not shown), while the foot portion (406) may be configured to interact with a ground surface (not shown) during use. In one example embodiment, as shown in FIG. 4B, the leg portion (404) may include a joint element (408) configured to movably couple with the device (402) such that the coupling provides the leg portion (404) with multiple degrees of freedom of movement relative to the foot portion (406) and ground surface.

To achieve an effective profile of impedance and stiffness for a given application (e.g., a prosthetic ankle), a certain number of cells in specific configurations may be energized using one or more magnetic fields, such as a magnetic field provided by electromagnet (410). In one example, an electromagnet ring (410) may include a wire coil and be positioned around or adjacent to the leg portion (404). Further, electromagnet (410) may be electrically coupled with a power source (412) for selectively driving the magnetic field from electromagnet (410).

To achieve time-varying impedance, as occurs in biological joints such as a human ankle, the magnetic field intensity of electromagnet (410) may be selectively controlled and varied in real-time, and/or the electromagnet (410) may be physically moved toward or away from the device (402) (see, FIG. 4A). As an alternative to electromagnet (410), other modes of magnetic field induction may be utilized, such as by using polymagnets (not shown) and a mechanism (not shown) configured to change their positions. Polymagnets are programmable permanent magnets that do not require continuous power consumption to achieve the desired profile and magnitude of the stiffness and damping in MR-based cells.

Figure 5:
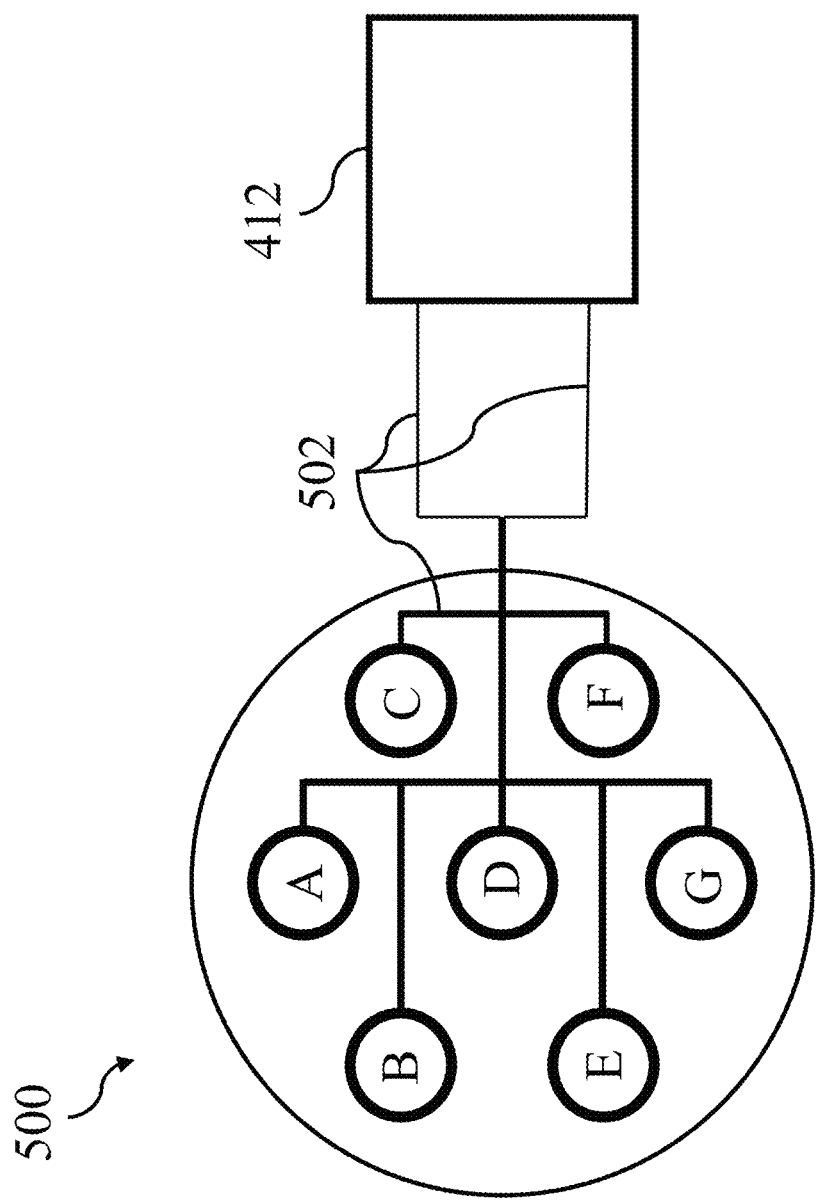
FIG. 5 depicts a schematic diagram of one exemplary alternative magnetic field inductor.
Figure 6:
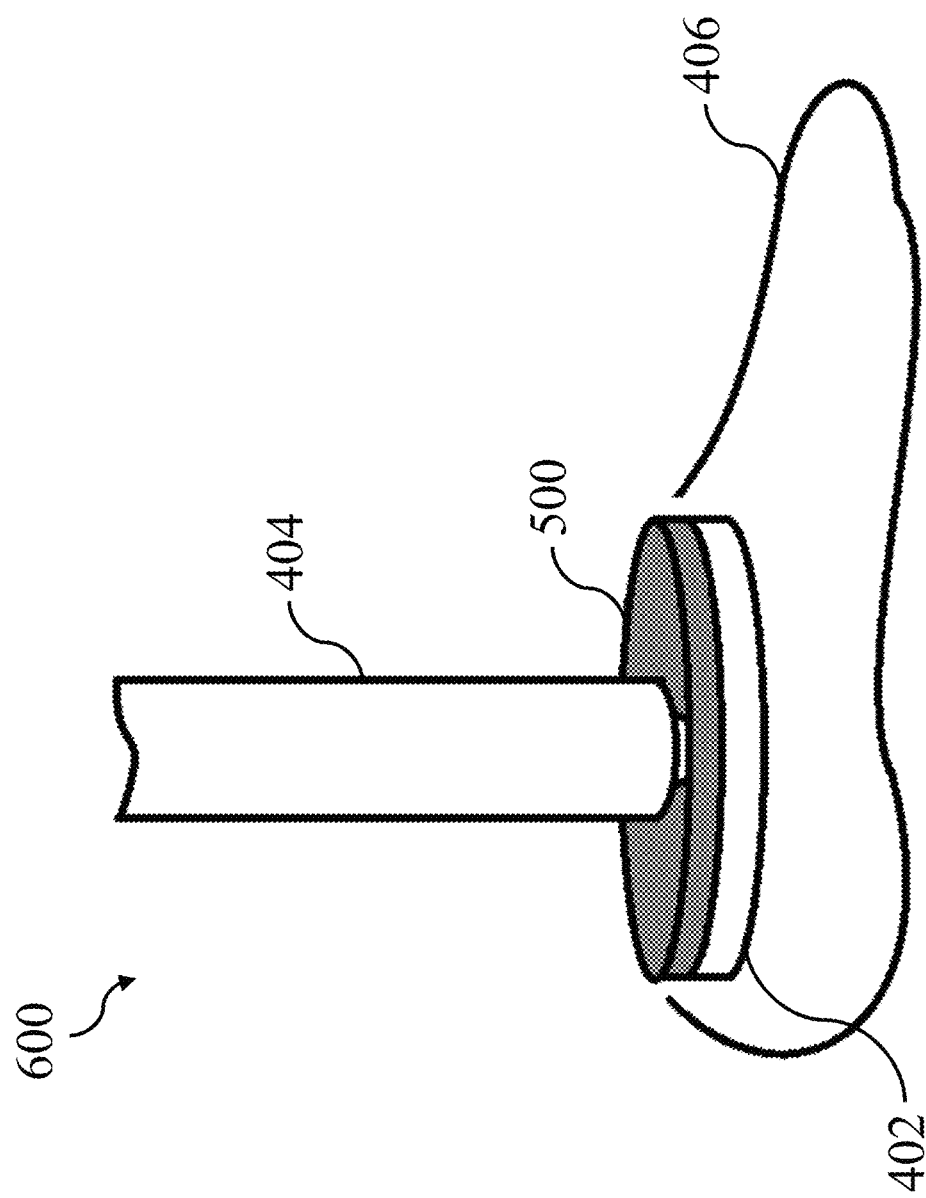
FIG. 6 depicts a schematic diagram of another example practical application of an MR fluid-based apparatus being used within an ankle prosthetic, showing the magnetic field inductor of FIG. 5 in use.

Shown in FIG. 5 is an electromagnetic element (500) which may be used as an alternative to electromagnet ring (410). To achieve greater operability of the MR fluid device (402), electromagnetic element (500) can include a plurality of electromagnets (elements A-G) each configured to be positioned over a respective MR fluid cell. In the embodiment shown by FIG. 5, each electromagnet (A-G) is operable to drive a separate magnetic field for one of the seven fluid cells as provided by MR fluid device (100). Additional electromagnets may be included as additional MR fluid cells are added. Accordingly, to drive the electromagnets (A-G), internal wiring (502) may be provided to element (500) for coupling with the power source (412). Element (500) may be positioned over the MR fluid device as shown in the application (600) of FIG. 6, in one example.

Figure 7:
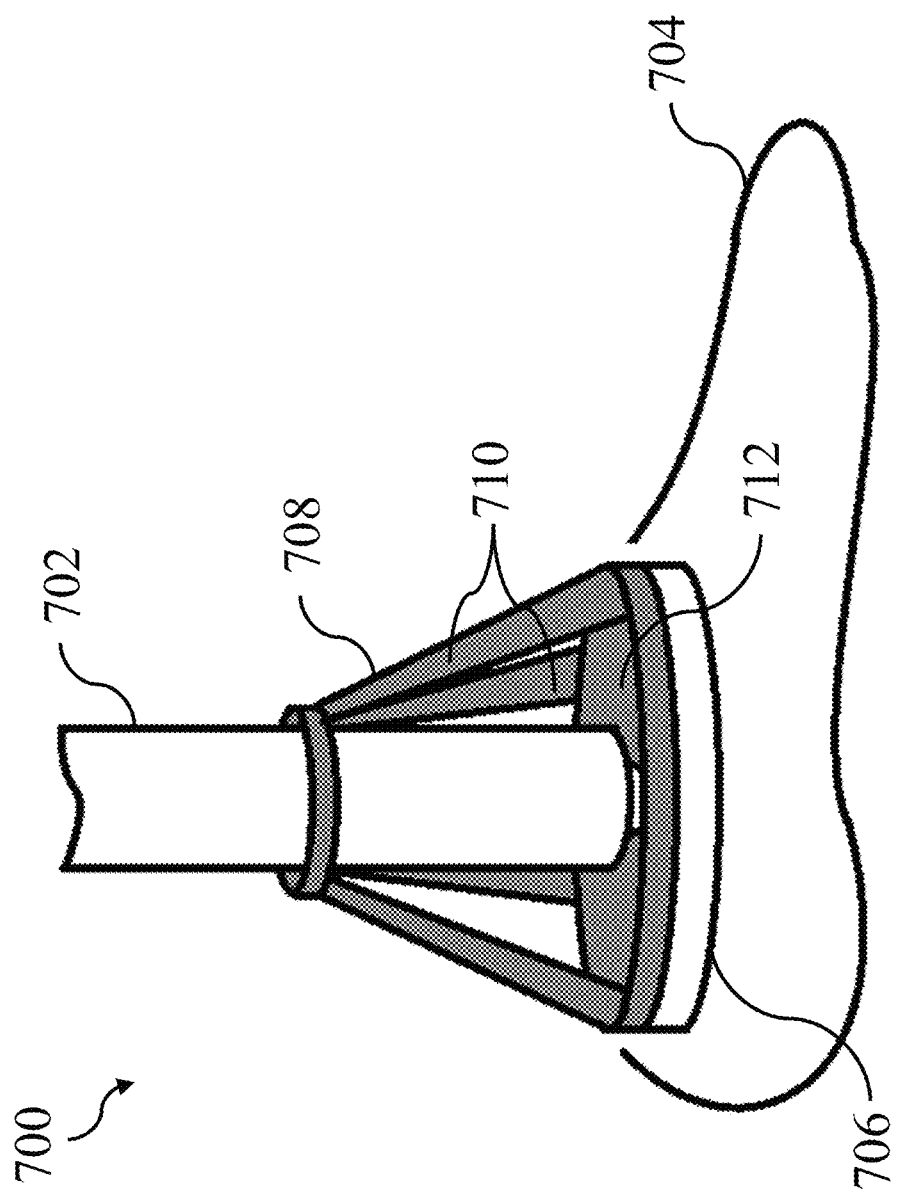
FIG. 7 depicts a schematic diagram of another example practical application of an MR fluid-based apparatus being used within an ankle prosthetic, showing a coupling for guiding the rotation of the leg portion with respect to the foot portion.

Shown in FIG. 7 is one exemplary version of an ankle prosthesis (700) having a leg portion (702), a foot portion (704), an MR fluid device (706), and a coupling element (708). The coupling element (708) may be fitted snug around the leg portion (702) and can include a rigid body having legs (710) which couple to a lower plate (712). An electromagnet (not shown), such as electromagnet ring (410) or electromagnetic element (500) may be utilized to vary the stiffness of the MR fluid device (706) as required during use of the ankle prosthesis (700). Accordingly, by varying the stiffness of the MR fluid device (706), the coupling element (708) will selectively restrict the degree of motion allowable between the leg portion (702) and the foot portion (704) as the MR fluid device (706) selectively allows different degrees of compression.

Figure 8:
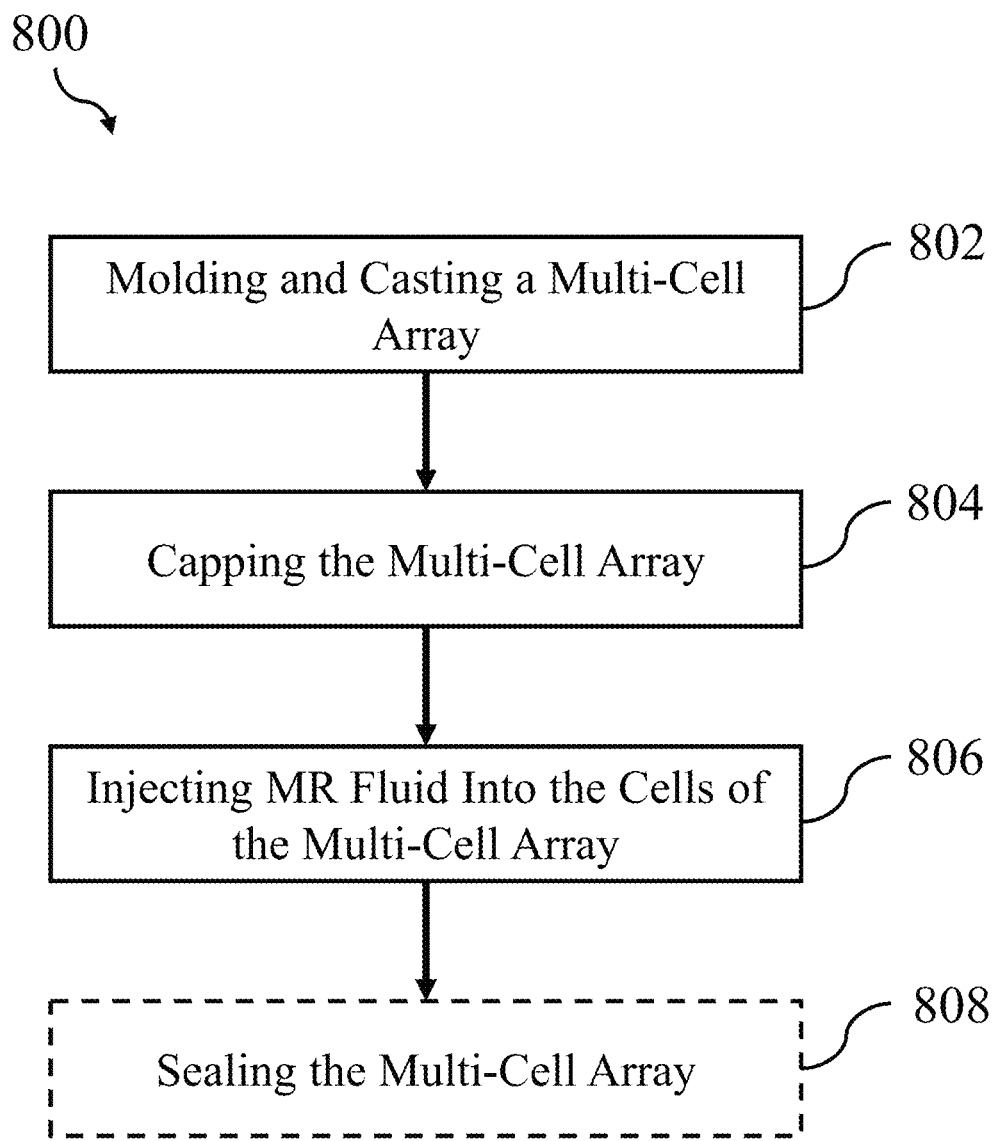
FIG. 8 depicts a flowchart of one exemplary method of manufacturing an MR fluid-based apparatus.

FIG. 8 provides one exemplary method (800) of manufacturing an MR fluid-based cell array, such as arrays (100, 200, 300) described above. Particularly, manufacturing or fabricating the MR fluid-based cell arrays can be divided into two general steps: (1) molding and shaping of the compliant matrix multi-cell array, and (2) introducing the MR fluid. Specifically, at step (802), molding and casting of the compliant matrix can be achieved in numerous ways as it would be done with any molding process. One exemplary process can includes: (a) creating computer graphics files such as computer aided designs (CADs) of negative molds; (b) 3D printing molding CADs to the best tolerances available; (c) applying casting spray so liquid rubber does not stick to 3D printed surfaces; (d) mixing liquid silicone rubber parts A and B (e.g., DRAGON SKIN branded high-performance silicone rubber manufactured by Smooth-On, Inc. of Macungie, PA) to have a curable mixture that turns into a solid rubber that is very compliant and high strain resistance; and (c) removing the casted silicone cell grid from 3D printed mold. When 3D printing molding CADs, negative molds can include holes on some parts to avoid trapped air bubbles. Further, thinner walls between cells, as described above, can increase relative stiffness increase under magnetization. Regarding mixing the liquid silicone rubber parts A and B, degassing the liquid silicone helps overall performance.

Next, at step (804), a top layer of silicone is created (e.g., through a similar molding process or otherwise) and is used to cap the multi-cell array such that each cell is closed to encapsulate air within. The top layer can in some processes be glued to the array using a silicone bonding glue.

Next, at step (806), MR fluid may be injected into each cell of the multi-cell array, such as by using a syringe as will be described in greater detail below. In some embodiments, a modified MR fluid may be utilized so as to be compatible with silicone rubber and prevent oil absorption by the silicone rubber matrix. MR fluids can also be modified to include added iron particles for higher rheological properties (i.e., stiffness and damping increase). Finally, at step (808), any holes made in the multi-cell array or capping layer may optionally be filled and sealed to prevent MR fluid leaking, if necessary. In some embodiments, a silicone bonding glue may be used for sealing.

Figure 9:
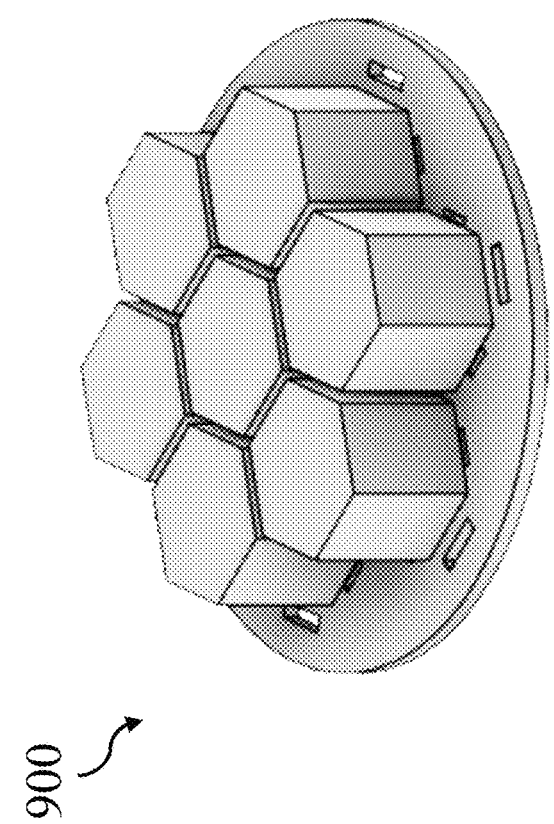
FIG. 9 depicts a schematic diagram of one exemplary negative mold for creating a first portion of the first MR fluid-based apparatus of FIG. 1A.
Figure 10:
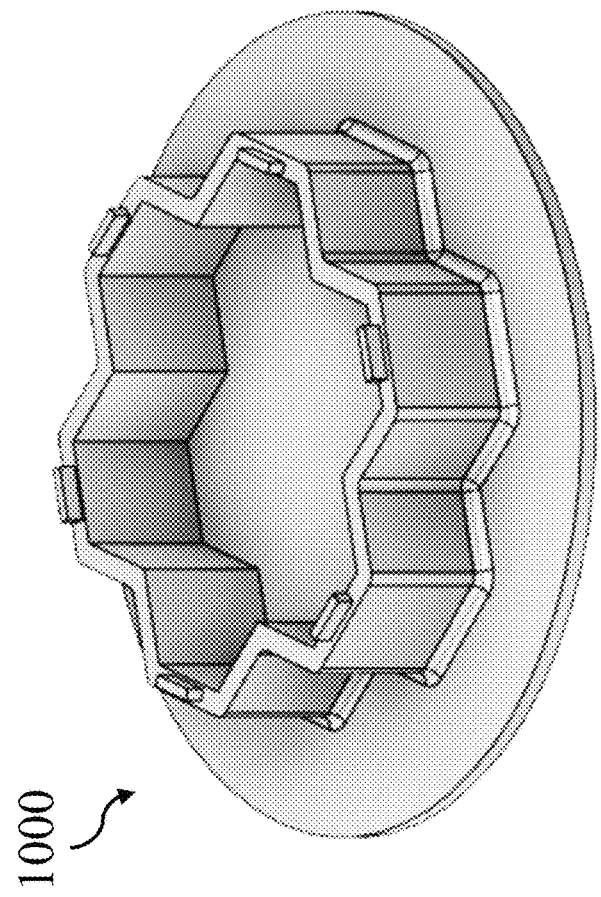
FIG. 10 depicts a schematic diagram of one exemplary negative mold for creating a second portion of the first MR fluid-based apparatus of FIG. 1A.
Figure 11:
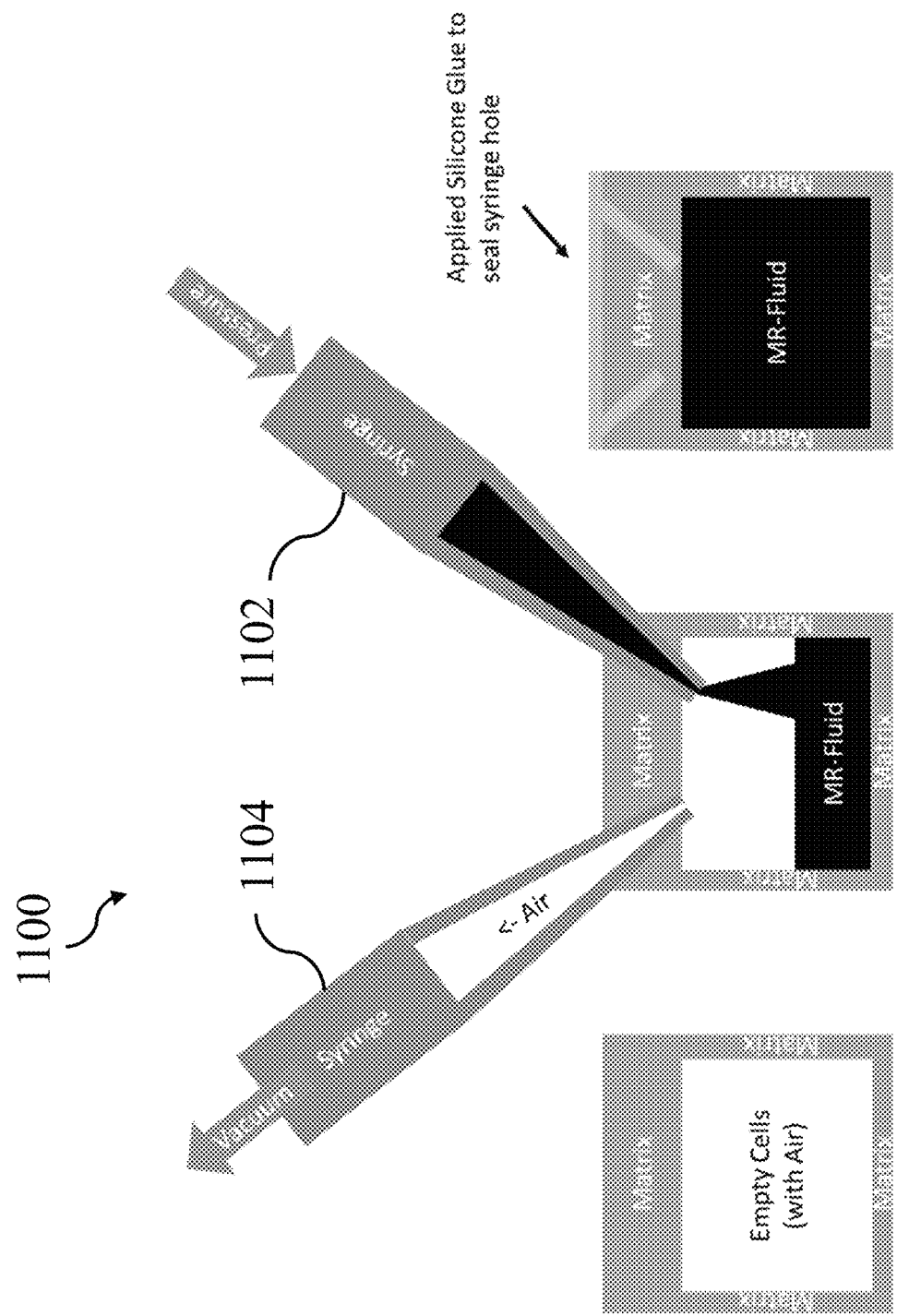
FIG. 11 depicts a block diagram of one exemplary process for injecting MR fluid into a cell of an MR fluid-based apparatus, showing a first syringe injecting the MR fluid into the cell and a second syringe extracting air from the cell.

Shown in FIG. 9 is one exemplary negative mold (900) which may be utilized to form the silicone rubber structure of the multi-cell array in accordance with step (802) of method (800) described above. Additionally, shown in FIG. 10 is one exemplary negative mold (1000) which may be utilized to form the capping layer for the multi-cell array. Particularly, molds (900, 1000) would be utilized to form a multi-cell array structure similar to MR fluid device (100) described above.

Shown in FIG. 10 is one exemplary process (1100) for injecting the MR fluid into each cell of the multi-cell array in accordance with step (806) of method (800) described above. Injection of the MR fluid provides advantageous overall structure and manufacturing consistency as compared to other methods. Further, injection of the MR fluid enables adjustment of the pressure of the fluid trapped in each cell. Further, if MR fluid is poured into open cells before attaching the top silicone layer, the MR fluid can in some instances interfere with the bonding agent and cause defects in the overall multi-cell array during use.

In the process (1100), a first syringe (1102) may be used to inject MR fluid into each cell of the multi-cell array. Further, it may be useful to have a second syringe (1104) to extract air out of the cells during injection to prevent creation of unwanted air pressure within the cell and causing MR fluid injection disturbances. The injection may be completed either through the capping layer side or through molded side of each cell. In an exemplary embodiment, the injection is completed through the capping layer as doing so can in some instances prevent rupture of the cell in the future and is easier to seal afterward.

In accordance with the description above, the feasibility, manufacturing, and design of multi-cell MR-fluid elastomer compounds are described with a maximum stiffness increase of at least two-fold. Particularly, the described devices can exhibit an axial compression stiffness increase of 250% or greater when compared to existing devices and can exhibit a rotational stiffness increase of 60% or greater. Further, the devices described herein provide quantitative and qualitative differences between the ankle impedance prior to push-off in dorsiflexion (D), plantarflexion (P), Inversion (I), and eversion (E) comparing a straight step and a turning step. The MR-based cells can be integrated into the design of an existing 2-DOF robotic ankle-foot prosthesis, allowing separation of its impedance modulation and torque control.

Additionally, the molds used to manufacture single-cell and multi-cell MR fluid-based arrays have been improved to enable thinner silicone elastomer walls. Thinner walls allow for greater stiffness contribution from the MR fluid viscous properties, thus allowing greater stiffness and damping modulation.

Reference systems that may be used herein can refer generally to various directions (for example, upper, lower, forward and rearward), which are merely offered to assist the reader in understanding the various embodiments of the disclosure and are not to be interpreted as limiting. Other reference systems may be used to describe various embodiments, such as those where directions are referenced to the portions of the device, for example, toward or away from a particular element, or in relations to the structure generally (for example, inwardly or outwardly).

While examples, one or more representative embodiments and specific forms of the disclosure have been illustrated and described in detail in the drawings and foregoing description, the same is to be considered as illustrative and not restrictive or limiting. The description of particular features in one embodiment does not imply that those particular features are necessarily limited to that one embodiment. Some or all of the features of one embodiment can be used in combination with some or all of the features of other embodiments as would be understood by one of ordinary skill in the art, whether or not explicitly described as such. One or more exemplary embodiments have been shown and described, and all changes and modifications that come within the spirit of the disclosure are desired to be protected.

We claim:
1. A magnetorheological joint system, comprising:
 (a) a first joint element;
 (b) a magnetorheological apparatus coupled with the first joint element, including:
  (i) a flexible body formed of a material including an elastomer;
  (ii) a plurality of cell cavities defined by the flexible body, wherein each cell cavity of the plurality of cell cavities is fluidly encapsulated within the flexible body;
  (iii) a magnetorheological (MR) fluid disposed within each cell cavity of the plurality of cell cavities; and
  (iv) a magnetic field inductor positioned adjacent to at least one of the cell cavities, wherein the magnetic field inductor is selectively operable to vary a magnetic field, wherein the MR fluid within the at least one cell cavity is configured to vary a stiffness of the at least one cell cavity in response to the magnetic field, and
 (c) a second joint element configured to movably contact the magnetorheological apparatus such that the magnetorheological apparatus provides multiple degrees of freedom of movement between the first joint element and the second joint element with variable stiffness.

2. The magnetorheological joint system of claim 1, comprising a power source selectively operable to provide a power signal to the magnetic field inductor to vary the magnetic field.

3. The magnetorheological joint system of claim 1, wherein the elastomer includes silicone rubber.

4. The magnetorheological joint system of claim 1, wherein the magnetic field inductor includes an electromagnet.

5. The magnetorheological joint system of claim 1, comprising a plurality of magnetic field inductors each positioned adjacent to one cell cavity of the plurality of cell cavities, wherein each magnetic field inductor is individually operable to provide an individualized magnetic field to vary the stiffness of each respective cell cavity in response to the individualized magnetic field.

6. The magnetorheological joint system of claim 1, wherein each cell cavity defines a hexagonal shape.

7. The magnetorheological joint system of claim 6, wherein each hexagonal cell cavity includes a plurality of sides, wherein at least one side of each cell cavity abuts another side of another cell cavity to form a shared wall, wherein shared wall thickness is 1.3 millimeters.

8. A magnetorheological apparatus, comprising:
(a) a flexible body formed including an elastomer material, wherein the flexible body includes a first portion defining a plurality of hexagonal cell cavities each having an open end and a second portion shaped to close the open end of each of the plurality of cell cavities, wherein each cell cavity of the plurality of cell cavities is fluidly encapsulated within the flexible body upon being closed using the second portion; and
(b) a magnetorheological (MR) fluid disposed within each cell cavity of the plurality of cell cavities, and
wherein a first side of the flexible body is configured to movably couple with a first articulated component and a second side of the flexible body is configured to movably couple with a second articulated component, wherein the magnetorheological apparatus is selectively operable to act as a joint having variable stiffness between the first articulated component and the second articulated component.

9. The magnetorheological apparatus of claim 8, wherein the elastomer includes silicone rubber.

10. The magnetorheological apparatus of claim 8, comprising a magnetic field inductor positioned adjacent to at least one of the cell cavities, wherein the magnetic field inductor is selectively operable to vary a magnetic field, wherein the MR fluid within the at least one cell cavity is configured to vary a stiffness of the at least one cell cavity in response to the magnetic field.

11. The magnetorheological apparatus of claim 8, comprising a plurality of magnetic field inductors each positioned adjacent to one cell cavity of the plurality of cell cavities, wherein each magnetic field inductor is individually operable to provide an individualized magnetic field to vary a stiffness of each respective cell cavity in response to the individualized magnetic field.

12. A method of manufacturing a magnetorheological apparatus, wherein the magnetorheological apparatus includes a flexible body, a plurality of cell cavities defined by the flexible body, and a magnetorheological (MR) fluid disposed within each cell cavity, the method comprising:

(a) providing a first articulated component and a second articulated component;
(b) molding the flexible body;
(c) casting the flexible body using an elastomeric material; and
(d) inserting the MR fluid into each cell cavity defined by the flexible body, wherein inserting the MR fluid includes puncturing the flexible body with a first syringe and injecting the magnetorheological fluid, and puncturing the flexible body with a second syringe, using the second syringe to simultaneously extract air from the cell cavity; and
(e) forming an articulable joint between the first articulated component and the second articulated component, including: (i) movably coupling a first side of the flexible body with the first articulated component; and (ii) movably coupling a second side of the flexible body with the second articulated component, wherein the magnetorheological apparatus comprising the flexible body is selectively operable to act as a joint having variable stiffness between the first articulated component and the second articulated component.

13. The method of claim 12, wherein molding the flexible body includes separately molding a first portion and a second portion, wherein casting the flexible body includes separately casting the first portion and the second portion, the method comprising: affixing the first portion to the second portion, wherein each cell cavity of the plurality of cell cavities is fluidly encapsulated within the flexible body upon affixing the first portion to the second portion.

14. The method of claim 12, wherein the flexible body includes silicone rubber.

15. The method of claim 12, wherein molding the flexible body includes forming the plurality of cell cavities each having a hexagonal shape.

16. The method of claim 15, wherein each hexagonal cell cavity includes a plurality of sides, wherein at least one side of each cell cavity abuts another side of another cell cavity to form a shared wall, wherein shared wall thickness is 1.3 millimeters.

17. The method of claim 12, comprising:
upon inserting the MR fluid into each cell cavity defined by the flexible body, sealing a hole created by the syringe through the flexible body.

18. The method of claim 12, comprising:
positioning a magnetic field inductor adjacent to at least one of the cell cavities.

19. The method of claim 18, comprising:
(a) coupling a power source to the magnetic field inductor; and
(b) configuring the magnetic field inductor to receive a power signal and, in response to the power signal, vary a magnetic field to adjust a stiffness of at least one cell cavity.

* * * * *